(12) United States Patent
Volz et al.

(10) Patent No.: US 9,169,198 B2
(45) Date of Patent: Oct. 27, 2015

(54) METHOD FOR THE PRODUCTION OF 2-AMINO-5-CYANO-N,3-DIMETHYLBENZAMIDE

(75) Inventors: Frank Volz, Köln (DE); Thomas Himmler, Odenthal (DE); Thomas Norbert Müller, Monheim (DE); Sandra Lehmann, Leverkusen (DE); Sascha Von Morgenstern, Burscheid (DE); Wahed Ahmed Moradi, Monheim (DE); Sergii Pazenok, Solingen (DE); Norbert Lui, Odenthal (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/131,114

(22) PCT Filed: Jul. 5, 2012

(86) PCT No.: PCT/EP2012/063167
§ 371 (c)(1),
(2), (4) Date: Jan. 6, 2014

(87) PCT Pub. No.: WO2013/007603
PCT Pub. Date: Jan. 17, 2013

(65) Prior Publication Data
US 2014/0148611 A1     May 29, 2014

Related U.S. Application Data

(60) Provisional application No. 61/506,263, filed on Jul. 11, 2011.

(30) Foreign Application Priority Data

Jul. 8, 2011   (EP) ..................................... 11173323

(51) Int. Cl.
| C07C 253/30 | (2006.01) |
| C07C 255/50 | (2006.01) |
| C07C 227/16 | (2006.01) |
| C07C 253/14 | (2006.01) |
| C07C 255/58 | (2006.01) |

(52) U.S. Cl.
CPC ............. *C07C 253/30* (2013.01); *C07C 227/16* (2013.01); *C07C 253/14* (2013.01); *C07C 255/58* (2013.01)

(58) Field of Classification Search
USPC ....................................................... 558/416
See application file for complete search history.

(56) References Cited

U.S. PATENT DOCUMENTS

| 5,716,993 A * | 2/1998 | Ozaki et al. .................... 514/619 |
| 8,034,968 B2 * | 10/2011 | Annis ........................... 558/415 |
| 8,049,029 B2 * | 11/2011 | Bruening et al. ............. 558/343 |
| 8,212,075 B2 * | 7/2012 | Grushin et al. ............... 564/124 |
| 8,242,279 B2 * | 8/2012 | Dumas ........................ 546/275.4 |
| 8,247,570 B2 * | 8/2012 | Dumas et al. .............. 546/276.1 |
| 8,748,630 B2 * | 6/2014 | Bruening et al. .......... 548/374.1 |
| 2004/0229900 A1 | 11/2004 | Alstermark et al. |
| 2010/0022780 A1 * | 1/2010 | Bruening et al. .......... 546/275.4 |
| 2010/0063287 A1 * | 3/2010 | Annis .............................. 546/4 |
| 2010/0280251 A1 * | 11/2010 | Bruening et al. .......... 546/276.1 |
| 2011/0003998 A1 * | 1/2011 | Dumas ........................ 546/275.4 |
| 2011/0034695 A1 * | 2/2011 | Grushin et al. ............ 546/275.4 |
| 2012/0130080 A1 * | 5/2012 | Dumas et al. .............. 546/276.1 |

FOREIGN PATENT DOCUMENTS

| WO | 2006/062978 A1 | 6/2006 |
| WO | 2008008252 | 1/2008 |
| WO | 2008/065508 A1 | 6/2008 |
| WO | 2008/070158 | 6/2008 |
| WO | 2008/082502 | 7/2008 |
| WO | 2009/006061 | 1/2009 |
| WO | 2009/061991 | 5/2009 |
| WO | 2009/085816 | 7/2009 |
| WO | 2009/085816 A1 | 7/2009 |
| WO | 2009/111553 A1 | 9/2009 |
| WO | 2009111553 | 9/2009 |
| WO | 2010/149359 A1 | 12/2010 |

OTHER PUBLICATIONS

Emmanuel A. Meyer et al., "Synthesis and In Vitro Evaluation of 2-Aminoquinazolin-4(3H)-one-Based Inhibitors for tRNA-Guanine Transglycosylase (TGT)," Helvetica Chimica Acta, 2004, 87: 1333-1356.
V.A. Snieckus et al., "Stereoslective Syntheses of Isoquinuclidones," J. Org. Chem., 1972, 37: 2845-2848.
Gwynn P. Ellis et al., "Cyanation of Aromatic Halides," Chem. Rev. ,1987, 87:779-794.
L. Friedman et al., "Dimethylformamide as a Useful Solvent in Preparing Nitriles from Aryl Halides and Cuprous Cyanide; Improved Isolation Techniques," J. Org. Chem., 1961, 26: 2522-2524.
Raymond L. Betts et al., "A Kinetic Study of the Ammonolysis of Phenylacetic Esters in Methanol Solution," J. Am. Chem. Soc., 1937, 59: 1568-1572.
Richard J. De Feoand et al., "An Improved Method of Synthesis of Secondary Amides from Carboxylic Esters," J. Org. Chem., 1963, 28: 2915-2917.
Thomas Hoegberg et al., "Cyanide as an Efficient and Mild Catalyst in the Aminolysis of Esters," J. Org. Chem., 1987, 52: 2033-2036.
International Search Report dated Nov. 30, 2012, issued in Application No. PCT/EP2012/063167.
International Search Report for PCT/EP2012/063167 Mailed Nov. 30, 2012.

* cited by examiner

*Primary Examiner* — Nyeemah A Grazier
(74) *Attorney, Agent, or Firm* — Miles & Stockbridge P.C.

(57) ABSTRACT

The present invention relates to a process for preparing 2-amino-5-cyano-N,3-dimethylbenzamide of formula (I)

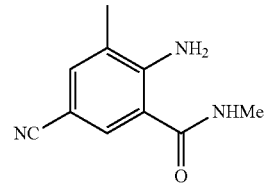

by reacting 2-amino-5-cyano-3-methylbenzoic esters or diesters with methylamine.

17 Claims, No Drawings

METHOD FOR THE PRODUCTION OF 2-AMINO-5-CYANO-N,3-DIMETHYLBENZAMIDE

CROSS REFERENCE TO RELATED APPLICATIONS

This application is a §371 National Stage Application of PCT/EP2012/063167, filed Jul. 5, 2012, which claims priority to European Application No. 11173323.4, filed Jul. 8, 2011, and claims benefit of U.S. Provisional Application No. 61/506,263, filed Jul. 11, 2011.

BACKGROUND

1. Field of the Invention

The present invention relates to a process for preparing 2-amino-5-cyano-N,3-dimethylbenzamide of formula (I)

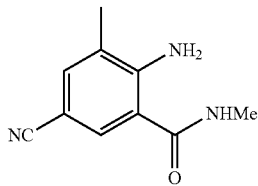

(I)

by reacting 2-amino-5-cyano-3-methylbenzoic esters or diesters with methylamine, for which the 2-amino-5-cyano-3-methylbenzoic esters or diesters are obtainable from the corresponding bromine compounds by cyanation with copper (I) cyanide. The bromine compounds are simple to prepare by brominating with a mixture of hydrogen bromide/hydrogen peroxide.

2. Description of Related Art

Preparation processes that also encompass the compound of formula (I) are already described in the literature (cf. for example WO 2008/08252, WO 2009/085816, WO 2009/006061, WO 2009/061991, WO 2009/111553, WO 2008/070158, WO 2008/082502) as leading to differing purity and yield.

The present invention accordingly has for its object to provide novel, economical processes for preparing 2-amino-5-cyano-N,3-dimethylbenzamide of formula (I) in higher purity, yield and better quality, especially by foregrounding the purification of the 2-amino-5-cyano-3-methylbenzoic esters or diesters needed for this.

SUMMARY

This object is achieved, in accordance with the present invention, by a process for preparing 2-amino-5-cyano-N,3-dimethylbenzamide of general formula (I)

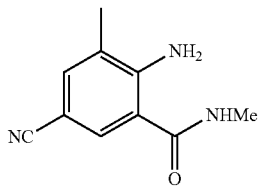

(I)

by reaction of 2-amino-5-cyano-3-methylbenzoic esters of formula (II)

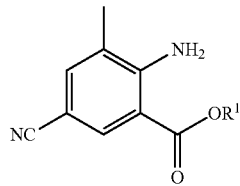

(II)

where
$R^1$ represents alkyl, cycloalkyl, alkoxyalkyl, arylalkyl, thioalkyl, alkylthioalkyl, alkylsulfonylalkyl, cyanoalkyl, haloalkyl, nitroalkyl or aryl,
$R^1$ preferably represents methyl, ethyl, $(C_5$-$C_{12})$alkyl or aryl,
$R^1$ more preferably represents methyl, ethyl, pentyl, hexyl or 2-ethylhexyl,
$R^1$ most preferably represents pentyl, hexyl or 2-ethylhexyl,
or by reaction of 2-amino-5-cyano-3-methylbenzoic diesters of formula (III)

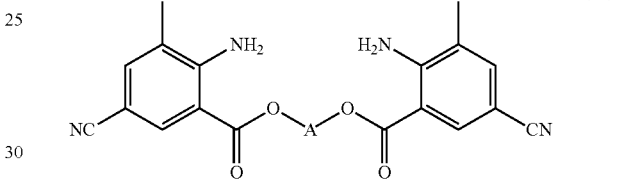

(III)

where
A represents alkylene and alkoxyalkylene,
A preferably represents methylene, ethylene or hexylene,
A more preferably represents ethylene or hexylene,
with $MeNH_2$ without further admixtures or by using at least one base such as sodium amide, sodium hydride, sodium hydroxide, sodium cyanide, potassium cyanide, potassium carbonate, sodium carbonate, caesium carbonate, sodium methoxide and triethylamine.

DETAILED DESCRIPTION OF A PREFERRED EMBODIMENT

The 2-amino-5-cyano-3-methylbenzoic esters or diesters of formulae (II) and (III) respectively are obtainable by reacting compounds of formula (IV) or of formula (V)

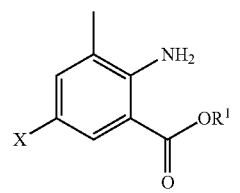

(IV)

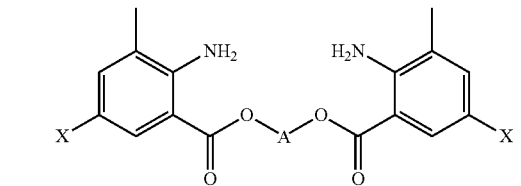

(V)

where in each case
X represents Br or I and A is as defined above,
with copper(I) cyanide.

The halogenated esters and diesters of general formulae (IV) and (V) are obtainable by reacting the compounds of general formulae (VI) and (VII)

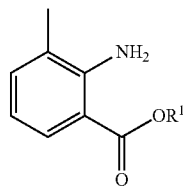
(VI)

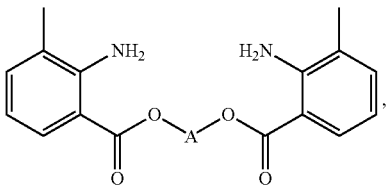
(VII)

where $R^1$ and A are as defined above,
with a mixture of hydrogen bromide and hydrogen peroxide.

The process of the present invention can be illustrated using the following scheme (I):

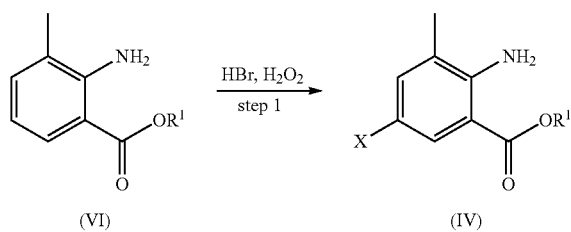

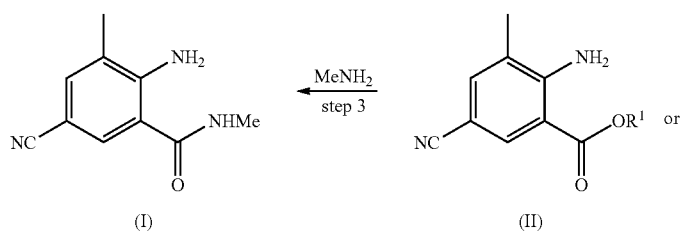

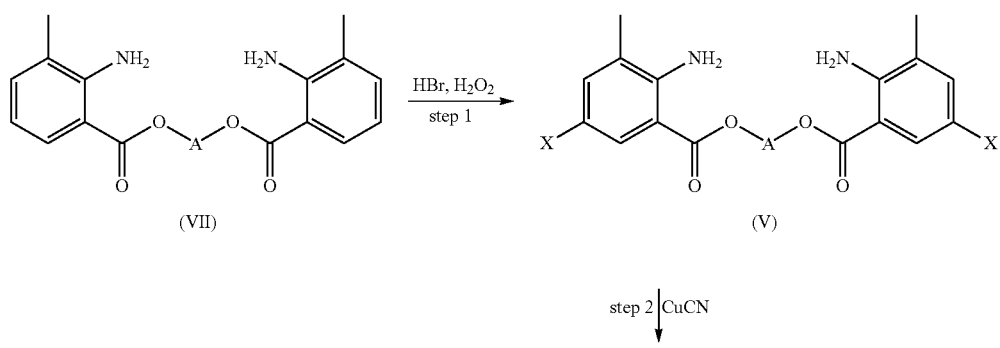

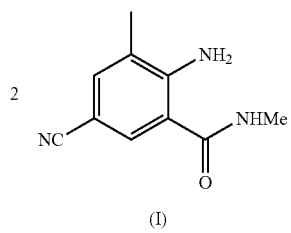

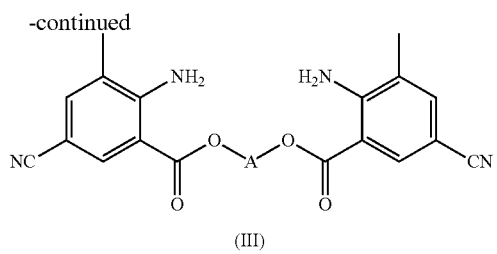

where R¹, X and A have the above-defined general meanings.

General Definitions:

In the context of the present invention, the term halogens (X) includes, unless defined differently, halogen elements selected from the group consisting of fluorine, chlorine, bromine and iodine, the use of fluorine, chlorine and bromine being preferable and of fluorine and chlorine particularly preferable. Substituted groups may be substituted with one or more substituents and these substituents may be the same or different when there are two or more of them.

Alkyl groups substituted with one or more halogen atoms (—X), i.e. haloalkyl groups, are for example selected from trifluoromethyl ($CF_3$), difluoromethyl ($CHF_2$), $CCl_3$, $CFCl_2$, $CF_3CH_2$, $ClCH_2$, $CF_3CCl_2$.

Alkyl groups in the context of the present invention, unless defined differently, are linear or branched hydrocarbon groups. Alkyl groups in the context of the present invention can be substituted one or more times by further groups in that, for example, cyanoalkyl groups are selected from cyanomethyl, cyano-ethyl, etc., nitroalkyl groups are selected for example from nitromethyl, nitroethyl, etc. Alkoxyalkyl groups are alkoxy-substituted alkyl groups, specific meanings including for example methoxymethyl, ethoxymethyl, propoxymethyl, etc.

The definition of alkyl and $C_1$-$C_{12}$-alkyl includes for example the meanings methyl, ethyl, n-propyl, isopropyl, n-butyl, isobutyl, sec-butyl and tert-butyl, n-pentyl, n-hexyl, 1,3-dimethylbutyl, 3,3-dimethylbutyl, n-heptyl, n-nonyl, n-decyl, n-undecyl, n-dodecyl.

Aryl radicals in the context of the present invention, unless defined differently, are aromatic hydrocarbon radicals which make one, two or more heteroatoms selected from O, N, P and S and may optionally be substituted by further groups.

Cycloalkyl groups in the context of the present invention, unless defined differently, are ring-shaped saturated hydrocarbon groups.

Arylalkyl groups and arylalkoxy groups in the context of the present invention, unless defined differently, are aryl-substituted alkyl and, respectively, alkoxy groups which may contain an alkylene chain. The definition of arylalkyl specifically includes for example the meanings benzyl and phenylethyl, and the definition of arylalkoxy includes for example the meaning benzyloxy.

Alkylene groups in the context of the present invention, unless defined differently, are linear or branched $C_1$-$C_{10}$ alkylene chains.

Step 1

Bromoanthranilic esters (X=Br) of formulae (IV) and (V) are obtainable as follows:

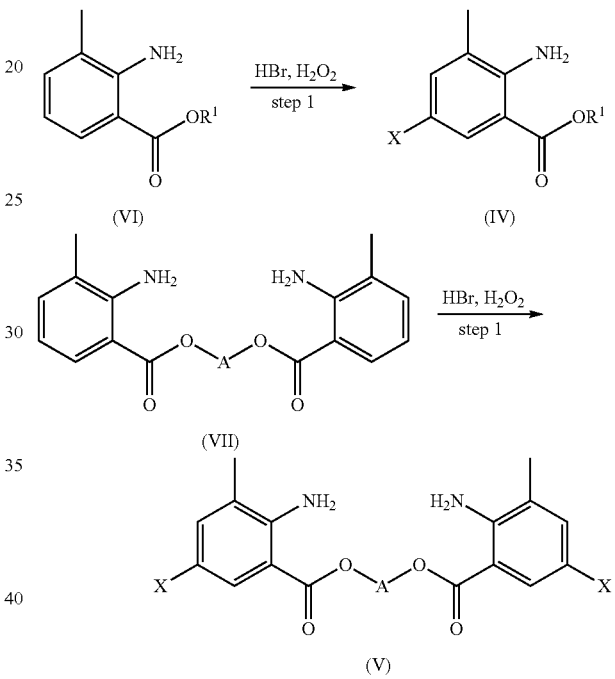

Anthranilic acid derivatives brominated in position 5 are usually prepared using elemental bromine in liquid or gaseous form (*Helv. Chim. Acta* 2004, 87, 1333-1356; WO 2008/065508; WO 2006/062978; WO 2008/070158; WO 2010/149359). Since, owing to HBr formulation, anthranilic esters are obtained in the form of corresponding ammonium bromides and require an additional purifying step for their release, it appears to be advantageous to use the combination of hydrogen bromide and hydrogen peroxide. The esters converted under this version were surprisingly obtained in very high purity and in high chemical yield, without troublesome hydrolysis and the expected ester cleavage. This conversion further merely requires water as solvent and nothing at all by way of admixtures such as acetic acid and the like, as described in the literature.

The process step of the present invention is preferably carried out within a temperature range of 40° C. to +120° C. and more preferably at temperatures of 40° C. to +80° C.

Process step (1) of the present invention is generally carried out under atmospheric pressure. Alternatively, however, it is also possible to employ reduced pressure or superatmospheric pressure.

Reaction time is uncritical and can be chosen as a function of batch size and temperature in a range between below one and two or more hours.

The process step of the present invention is carried out by using, per 1 mol of ester of formula (VI) or (VII), from 0.8 mol to 1.4 mol, preferably from 0.9 mol to 1.2 mol and more preferably 1.05 mol of hydrogen bromide and from 0.8 mol to 1.4 mol, preferably from 0.9 mol to 1.2 mol and more preferably 1.1 mol of hydrogen peroxide.

Examples of suitable solvents are aliphatic, alicyclic or aromatic halogenated hydrocarbons, e.g. chlorobenzene, dichlorobenzene, dichloromethane, chloroform, tetrachloromethane, dichloroethane or trichloroethane, nitriles, such as acetonitrile, propionitrile, n- or isobutyronitrile or benzonitrile and water, aliphatic or alicyclic carboxylic acids. Particular preference is given to using chlorobenzene, dichlorobenzene, dichloromethane, chloroform, dichloroethane, trichloroethane, acetic acid, propionic acid, butanoic acid, acetonitrile, butyronitrile and water.

The brominated products are removable from the two-phase system without prior work-up, either by filtration from the aqueous phase or, depending on the melting point of the product obtained, in the form of the melt. The products obtained can be used in the subsequent step (2), in which the cyanation takes place, without further purification.

Step 2

Cyanoanthranilic esters of formulae (IV) and (V) are obtainable as follows:

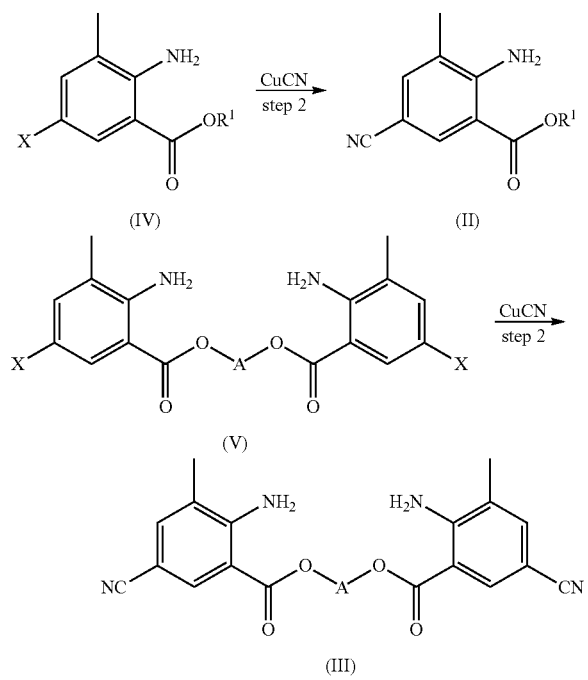

It is known from the literature that cyanoanthranilic esters are obtainable by converting 5-halogenated anthranilic acid derivatives using catalytic amounts of palladium, nickel and copper catalysts in the presence of various diamine, pyridine and phosphine ligands (WO 2008/070158 A1, WO 2008/082502 A2, WO 2009/006061 A2, WO 2009/061991 A1, WO 2009/085816 A1, WO 2009/111553 A1). However, these processes have the following disadvantages: The homogeneous catalysts based on palladium, nickel and copper are usually difficult to remove from the product to be isolated and hence also very difficult to recycle. The same holds for the ligands used. Nickel catalysts, moreover, are toxicologically concerning if they end up as an impurity in the product. The consequence is often a need for costly and inconvenient purification. Palladium and nickel catalysis, what is more, usually proceeds with some dehalogenation and the aromatic species has a proton in place of the expected cyanide. Nor are there any examples in the literature of cyanations of alkyl 2-amino-5-bromo-3-methylbenzoates using stoichiometric amounts of copper(I) cyanide. There is only one experimentally verified cyanation of ethyl 2-amino-5-bromo-3-ethylbenzoate: V. A. Sniekus et al. *J. Org. Chem.* 1972, 37, 2845-2848. Purification often requires costly and inconvenient operations (G. P. Ellis et al., *Chem. Rev.* 1987, 87, 779-794; Friedman, Schechter, *J. Org. Chem.* 1961, 26, 2522-2524). The substitution patterns depicted in formula (II) for R=$C_1$-$C_4$alkyl are already described in the following references: WO 2008/070158 A1, WO 2008/082502 A2, WO 2009/006061 A2, WO 2009/061991 A1, WO 2009/085816 A1, WO 2009/111553 A1. These unexamined applications, however, do not describe any experimentally verified examples of a bromine-cyano exchange on an anthranilic ester of formula (IV) or (V). The inventors found that, surprisingly and in contrast to the processes described above, the use of stoichiometric copper (I) cyanide in N,N-dimethylformamide, N,N-dimethylacetamide, N-methylformanilide, N-methylpyrrolidone, hexamethylphosphoramide and dimethyl sulphoxide as solvent gives rise to a selective reaction which, after isolation by removing the copper salts with aqueous ammonia, provides the cyanated esters of formulae (II) and (III) in good yields coupled with appropriate purity.

The process step of the present invention is preferably carried out within a temperature range of 100° C. to +200° C. and more preferably at temperatures of 140° C. to +180° C.

Process step (2) of the present invention is generally carried out under atmospheric pressure. Alternatively, however, it is also possible to employ reduced pressure or superatmospheric pressure.

Reaction time is uncritical and can be chosen as a function of batch size and temperature in a range between below one and two or more hours.

The process step of the present invention is carried out by using, per 1 mol of ester of formula (IV) or (V), from 0.8 mol to 1.4 mol, preferably from 0.9 mol to 1.2 mol and more preferably 1.00 mol of copper(I) cyanide.

Examples of suitable solvents are aliphatic, alicyclic or aromatic halogenated hydrocarbons, e.g. chlorobenzene, dichlorobenzene, dichloromethane, chloroform, tetrachloromethane, dichloroethane or trichloroethane, ethers, such as 1,2-dimethoxyethane, 1,2-diethoxyethane or anisole; nitriles, such as benzonitrile; amides, such as N,N-dimethylformamide, N,N-dimethylacetamide, N-methylformanilide, N-methylpyrrolidone or hexamethylphosphoramide; sulphoxides, such as dimethyl sulphoxide or sulphones, such as sulpholane; pyridine derivatives, such as pyridine, 2-methyl-5-ethylpyridine, 2-picoline, 3-picoline, particular preference being given to using N,N-dimethylformamide, N,N-dimethylacetamide, N-methylformanilide, N-methylpyrrolidone, pyridine, 2-methyl-5-ethylpyridine, 2-picoline, 3-picoline.

The cyanated products of formulae (II) and (III) are initially obtained as copper complexes and can be decomplexed by washing with aqueous ammonia, ethylenediamine, ethylenediaminetetraacetic acid (EDTA), aqueous iron(III) chloride and be isolated either from the aqueous solid obtained or extractively using suitable solvents. The products obtained of formulae (II) and (III) can be used in the subsequent step (3), in which the aminolysis takes place, without further purification.

Step 3

2-Amino-5-cyano-N,3-dimethylbenzamide of formula (I) is obtainable as follows:

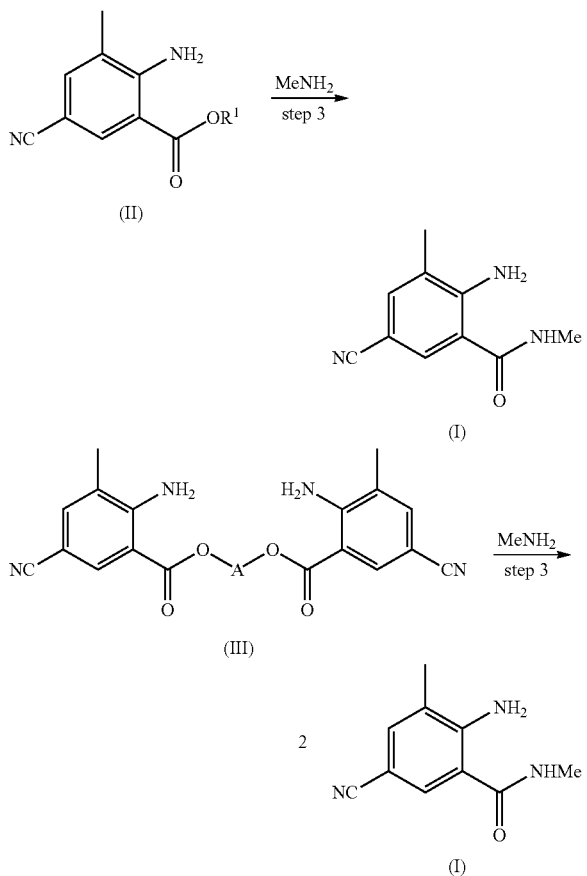

2-Amino-5-cyano-N,3-dimethylbenzamide of formula (I) is obtainable in high yield and purity by reacting appropriate 2-amino-5-cyano-3-methylbenzoic esters of formula (II) or diesters of formula (III) with methylamine with or without catalytic admixture of a base. The literature describes aminolyses by admixture of sodium methoxide: R. L. Betts et al., J. Am. Chem. Soc. 1937, 59, 1568-1572; R. J. de Feoand et al., J. Org. Chem. 1963, 28, 2915-2917, sodium amide, sodium hydride, Grignard reagents and butyllithium as base: refs 4-8 in T. Högberg, J. Org. Chem. 1987, 52, 2033-2036. Sodium cyanides are also described as a base for aminolyses in the literature (T. Högberg, J. Org. Chem. 1987, 52, 2033-2036). Aminolyses of cyanoanthranilic acid derivatives are already described in WO 2006/062978, albeit without experimental verifications. The reaction of cyanoanthranilic esters with methylamine in methanol by admixture of sodium methoxide was observed to proceed to complete conversion coupled with high yield and purity. The reaction can also be carried out without admixture of sodium methoxide. Moreover, there is no attack on the nitrile functionality to form undesired by-products.

The process step of the present invention is preferably carried out within a temperature range of 20° C. to +100° C., preferably at temperatures of 20° C. to 80° C. and more preferably at temperatures of 20° C. to 60° C.

Process step (3) of the present invention is generally carried out under atmospheric pressure. Alternatively, however, it is also possible to employ superatmospheric pressure.

The reaction time is uncritical and can be chosen as a function of batch size and temperature in the range between below one and two or more hours.

The reaction is preferably carried out batchwise. However, continuous reaction procedures are likewise possible.

The process step of the present invention is carried out using, per 1 mol of ester of formula (IV) or (V), from 2 mol to 20 mol, preferably from 5 mol to 15 mol and more preferably 10 mol of methylamine.

The reaction can be carried out without admixing a base. If a base is used, the following are suitable: e.g. sodium hydroxide, potassium carbonate, sodium carbonate, caesium carbonate, sodium methoxide, sodium amide, Grignard reagents, butyllithium, triethylamine, diisopropylethylamine or sodium hydride. Particular preference is given to alkoxide bases (ROM, R=alkyl, M=Na, K), sodium hydroxide and potassium hydroxide.

Any solvent that is substantially inert under reaction conditions can be used, examples being aliphatic, alicyclic or aromatic halogenated hydrocarbons, e.g. chlorobenzene, dichlorobenzene, dichloromethane, chloroform, tetrachloromethane, dichloroethane or trichloroethane, ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutylnitrile or benzonitrile; amides, such as N,N-dimethylformamide, N,N-dimethylacetamide, N-methylformanilide, N-methylpyrrolidone or hexamethylphosphoramide; sulphoxides, such as dimethyl sulphoxide or sulphones, such as sulpholane, alcohols such as methanol, ethanol, isopropanol, and also solvent mixtures. Particular preference is given to using acetonitrile, methanol, ethanol, isopropanol and butyronitrile.

The 2-amino-5-cyano-N,3-dimethylbenzamide comes down as a precipitate at the end of the reaction and is obtainable by filtration in yields of about 82-90% coupled with purities of about 93-95 weight % HPLC.

PREPARATION EXAMPLES

The preparation examples which follow illustrate the invention without restricting it.

Example 1

Methyl 2-amino-3-methylbenzoate $^1$H NMR (600 MHz, (d$^6$-DMSO): δ=7.64 (dd, 1H), 7.19 (d, 1H), 6.50 (pq, 3H, Ar—H, NH2), 3.79 (s, 3H), 2.12 (s, 3H)).

Methyl 2-amino-5-bromo-3-methylbenzoate

A solution of methyl 2-amino-3-methylbenzoate (142.1 g, 0.843 mol, purity: 98% quantitative NMR) in 240 mL of H$_2$O is gradually admixed at 30° C. with hydrogen bromide (48% of H$_2$O, 149.2 g, 0.885 mol) added dropwise. The suspension obtained is admixed with hydrogen peroxide (30% in H$_2$O, 105.1 g, 0.927 mol) added dropwise over 2 h, and the temperature is kept below 70° C. After 1 hour of subsequent stirring, NaHSO$_3$ (39% in H$_2$O, 33.7 g, 0.126 mol) is added a little at a time (peroxide test was negative). The suspension obtained is adjusted to pH7-8 with Na$_2$CO$_3$ (0.1 eq., 9.0 g, 0.084 mol), which is added a little at a time. Following filtration and drying in a vacuum drying cabinet, methyl 2-amino-5-bromo-3-methylbenzoate is isolated as a pale brown solid.

Yield: 204.2 g, 97.7% of theory, purity: 98.5% quantitative NMR).

$^1$H NMR (600 MHz, (d$^6$-DMSO): δ=7.70 (d, 1H), 7.36 (pt, 1H), 6.63 (br s, 2H), 3.80 (s, 3H), 2.12 (s, 3H)).

The above-described method (Example 1) was repeated to react pentyl 2-amino-3-methylbenzoate (2.28 g, 10 mmol) with hydrogen bromide (2.21 g, 13 1 mmol, 48% in water) and hydrogen peroxide (1.72 g, 15.0 mmol, 30% in water). Following working up similar to Example 1 and additional column chromatography, pentyl 2-amino-5-bromo-3-methylbenzoate (2.7 g, 88.3% of theory, >99 area% LC) was obtained as a yellow solid.

$^1$H NMR (600 MHz, (CD$_3$CN): δ=7.81 (d, 1H), 7.32 (pt, 1H), 6.10 (br s, 2H), 4.23 (t, 2 H), 2.12 (s, 3H), 1.74 (m, 2H), 1.45 (m, 4H), 0.93 (m, 3H)).

The above-described method (Example 1) was repeated to react hexyl 2-amino-3-methylbenzoate (2.50 g, 10 mmol) with hydrogen bromide (2.21 g, 13 1 mmol, 48% in water) and hydrogen peroxide (1.72 g, 15.0 mmol, 30% in water). Following working up similar to Example 1 and additional column chromatography, hexyl 2-amino-5-bromo-3-methylbenzoate (2.5 g, 78.8% of theory, >99 area % LC) was obtained as a brown oil.

$^1$H NMR (600 MHz, (CD$_3$CN): δ=7.80 (d, 1H), 7.31 (d, 1H), 6.10 (br s, 2H), 4.23 (t, 2 H), 2.12 (s, 3H), 1.73 (m, 2H), 1.46 (m, 6H), 0.91 (m, 3H)).

The above-described method (Example 1) was repeated to react 2-ethylhexyl 2-amino-3-methylbenzoate (3.00 g, 10.6 mmol) with hydrogen bromide (2.33 g, 13 8 mmol, 48% in water) and hydrogen peroxide (1.81 g, 15.9 mmol, 30% in water). Following working up similar to Example 1 and additional column chromatography, 2-ethylhexyl 2-amino-5-bromo-3-methylbenzoate (2.7 g, 74.0% of theory, >99 area % LC) was obtained as a brown oil.

$^1$H NMR (600 MHz, (CD$_3$CN): δ=7.79 (d, 1H), 7.32 (d, 1H), 6.11 (br s, 2H), 4.17 (d, 2H), 2.13 (s, 3H), 1.70 (m, 7H), 0.94 (m, 7H)).

The above-described method (Example 1) was repeated to react 2-ethyl 2-amino-3-methylbenzoate (16.29 g, 90.0 mmol) with hydrogen bromide (15.93 g, 94.5 mmol, 48% in water) and hydrogen peroxide (11.25 g, 99.0 mmol, 30% in water) and, following working up similar to Example 1, ethyl 2-amino-5-bromo-3-methylbenzoate (20.7 g, 89.1% of theory, >99 area % LC) was obtained as a brown oil.

$^1$H NMR (600 MHz, (CD$_3$CN): δ=7.81 (d, 1H), 7.32 (pq, 1H), 6.10 (br s, 2H), 4.28 (q, 2H), 1.34 (t, 3H)).

The above-described method (Example 1) was repeated to react ethane-1.2-diyl 2-amino-3-methylbenzoate (2.0 g, 5.89 mmol) with hydrogen bromide (2.09 g, 12.3 mmol, 48% in water) and hydrogen peroxide (1.47 g, 12.9 mmol, 30% in water) and, following working up similar to Example 1, ethane-1,2-diyl 2-amino-5-bromo-3-methylbenzoate (2.4 g, 80.0% of theory, 95.5 area % LC) was obtained as a pale yellow solid.

$^1$H NMR (600 MHz, (d$^6$-DMSO): δ=7.71 (d, 1H), 7.36 (d, 1H), 6.63 (br s, 2H), 4.56 (s, 2H), 2.11 (s, 3H)).

The above-described method (Example 1) was repeated to react hexane-1,6-diyl 2-amino-3-methylbenzoate (4.0 g, 10.4 mmol) with hydrogen bromide (3.57 g, 21.1 mmol, 48% in water) and hydrogen peroxide (2.52 g, 22 1 mmol, 30% in water) and, following working up similar to Example 1, hexane-1,6-diyl 2-amino-5-bromo-3-methylbenzoate (5.36 g, 90.9% of theory, 92.6 area % LC) was obtained as a brown solid.

$^1$H NMR (600 MHz, (d$^6$-DMSO): δ=7.69 (d, 1H), 7.35 (d, 1H), 6.63 (br s, 2H), 4.22 (t, 2H), 2.11 (s, 3H), 1.73 (m, 2H), 1.45 (m, 2H)).

The above-described method (Example 1) was repeated to react 2-methoxyethyl 2-amino-3-methylbenzoate (7.00 g, 33.4 mmol) with hydrogen bromide (5.92 g, 35.1 mmol, 48% in water) and hydrogen peroxide (4.17 g, 36.7 mmol, 30% in water) and, following working up similar to Example 1, 2-methoxyethyl 2-amino-5-bromo-3-methylbenzoate (8.50 g, 80.7% of theory, 91.5 area % LC) was obtained as a brown solid.

$^1$HNMR (600 MHz, (d$^6$-DMSO): δ=7.70 (d, 1H), 7.37 (d, 1H), 6.63 (br s, 2H), 4.34 (t, 2H), 3.65 (t, 2H), 3.31 (s, 3H), 2.10 (s, 3H)).

A solution of methyl 2-amino-5-bromo-3-methylbenzoate (5 g, 20.4 mmol) in benzyl alcohol (4.43 g, 40.9 mmol) and sodium methoxide (0.37 g, 2.04 mmol, 30% in methanol) was refluxed in xylene (10 ml) for 5 hours. Then, water was added, the phases were separated and the combined organic solvents were removed in vacuo. The residue was purified by column chromatography to obtain benzyl 2-amino-5-bromo-3-methylbenzoate (3.40 g, 43.3% of theory, 83.6 area % GC) as a pale brown solid.

$^1$H NMR (600 MHz, (CDCl$_3$): δ=7.92 (s, 1H), 7.44-7.28 (m, 6H), 5.86 (s, 2H), 5.33 (s, 2H), 2.14 (s, 3H)).

Example 2

Methyl 2-amino-5-bromo-3-methylbenzoate (100 g, 0.393 mol, 96% of quantitative NMR), copper(I) cyanide (36.3 g, 0.401 mol) and N-methyl-2-pyrrolidinone (NMP) (206 g, 200 mL, 2.084 mol) are heated to 170° C. for 4 hours under agitation. The reaction batch is cooled down to 120° C., 350 mL of H$_2$O (90° C.) are added dropwise in the course of 30 minutes and the suspension obtained is filtered. The solid obtained is washed twice with ammonia (200 g, 12% in H$_2$O) and 2 times with 100 ml of water. Following drying in a vacuum drying cabinet at 50° C., methyl 2-amino-5-cyano-3-methylbenzoate is obtained as a grey solid. Yield: 69.0 g, 88.2% of theory, purity: 95.6% quantitative NMR, 1500 ppm Cu).

$^1$H NMR (600 MHz, (MeOD): δ=8.04 (d, 1H), 7.40 (m, 1H), 4.85 (s, 3H), 2.18 (s, 3H)).

The above-described method (Example 2) was repeated to react pentyl 2-amino-5-bromo-3-methylbenzoate (2.3 g, 7.59 mmol) with copper cyanide (0.69 g, 7.74 mmol) in N,N-dimethylacetamide at 170° C. for 6 hours. Following working up similar to Example 2 and additional extraction with ethyl acetate and washing with aqueous 5% ethylenediamine solution, pentyl 2-amino-5-cyano-3-methylbenzoate (1.78 g, 89.2% of theory, 93.6 area % LC) was obtained as a brown oil.

$^1$H NMR (600 MHz, (CD$_3$CN): δ=8.08 (d, 1H), 7.43 (s, 1H), 6.67 (br s, 2H), 4.24 (t, 2H), 2.15 (s, 3H), 1.75 (m, 2H), 1.40 (m, 4H), 1.05 (m, 3H)).

The above-described method (Example 2) was repeated to react hexyl 2-amino-5-bromo-3-methylbenzoate (2.2 g, 6.79 mmol) with copper cyanide (0.62 g, 6.93 mmol) in N,N-dimethylacetamide at 170° C. for 6 hours. Following working up similar to Example 2 and additional extraction with ethyl acetate and washing with aqueous 5% ethylenediamine solution, hexyl 2-amino-5-cyano-3-methylbenzoate (1.66 g, 85.5% of theory, 91.1 area % LC) was obtained as a brown oil.

$^1$H NMR (600 MHz, (CD$_3$CN): δ=8.08 (d, 1H), 7.43 (s, 1H), 6.67 (br s, 2H), 4.24 (t, 2H), 2.14 (s, 3H), 1.74 (m, 2H), 1.39 (m, 6H), 0.92 (m, 3H)).

The above-described method (Example 2) was repeated to react 2-ethylhexyl 2-amino-5-bromo-3-methylbenzoate (2.00 g, 5.84 mmol) with copper cyanide (0.53 g, 5.96 mmol) in N,N-dimethylacetamide at 160° C. for 8 hours. Following working up similar to Example 2 and additional washing with aqueous 5% ethylenediamine solution, 2-ethylhexyl 2-amino-5-cyano-3-methylbenzoate (1.45 g, 76.7% of theory, 89.1 area % LC) was obtained as a brown oil.

$^1$H NMR (400 MHz, CD$_3$CN): δ=8.06 (d, 1H), 7.43 (s, 1H), 6.70 (br. s, 2H), 4.19 (d, 2H), 2.15 (s, 3H), 1.71 (m, 1H), 1.39 (m, 8 H), 0.90 (m, 6H).

The above-described method (Example 2) was repeated to react ethyl 2-amino-5-bromo-3-methylbenzoate (2.00 g, 7.65 mmol) with copper cyanide (0.70 g, 7.80 mmol) in N,N-dimethylacetamide at 160° C. for 8 hours. Following working up similar to Example 2, ethyl 2-amino-5-cyano-3-methylbenzoate (1.30 g, 80.2% of theory, 96.3 area % LC) was obtained as a brown solid.

$^1$H NMR (400 MHz, CD$_3$CN): δ=8.09 (d, 1H), 7.43 (s, 1H), 6.68 (br. s, 2H), 4.30 (q, 2H), 2.13 (s, 3H), 1.35 (t, 3H).

The above-described method (Example 2) was repeated to react ethane-1,2-diyl 2-amino-5-bromo-3-methylbenzoate (2.00 g, 3.94 mmol) with copper cyanide (0.72 g, 8.07 mmol) in N-methylpyrrolidone at 170° C. for 4 hours. Following working up similar to Example 2 and additional washing with aqueous 5% ethylenediamine solution, ethane-1.2-diyl 2-amino-5-cyano-3-methylbenzoate (1.54 g, 81.9% of theory, 79.2 area % LC) was obtained as a brown solid.

$^1$H NMR (600 MHz, d$^6$-DMSO): δ=8.00 (d, 1H), 7.54 (s, 1H), 7.27 (br s, 2H), 4.60 (s, 2H), 2.12 (s, 3H).

The above-described method (Example 2) was repeated to react hexane-1.6-diyl 2-amino-5-bromo-3-methylbenzoate (4.00 g, 6.86 mmol) with copper cyanide (1.29 g, 14.06 mmol) in N-methylpyrrolidone at 170° C. for 4 hours. Following working up similar to Example 2 and additional washing with aqueous 5% ethylenediamine solution, hexane 1,2-diyl 2-amino-5-cyano-3-methylbenzoate (3.20 g, 82.7% of theory, 77.0 area % LC) was obtained as a brown solid.

$^1$H NMR (600 MHz, (d$^6$-DMSO): δ=7.98 (d, 1H), 7.53 (s, 1H), 7.28 (br s, 2H), 4.25 (t, 2H), 2.14 (s, 3H), 1.74 (m, 2H), 1.46 (m, 2H).

The above-described method (Example 2) was repeated to react 2-methoxyethyl 2-amino-5-bromo-3-methylbenzoate (5.00 g, 15.88 mmol) with copper cyanide (1.49 g, 16.67 mmol) in N-methylpyrrolidone at 170° C. for 6 hours. Following working up similar to Example 2 and additional extraction with ethyl acetate and washing with aqueous 5% ethylenediamine solution, 2-methoxyethyl 2-amino-5-cyano-3-methylbenzoate (0.45 g, 11.6% of theory, 95.6 area % LC) was obtained as a brown solid.

$^1$H NMR (600 MHz, (CD$_3$CN): δ=8.08 (d, 1H), 7.45 (s, 1H), 6.67 (br s, 2H), 4.38 (t, 2H), 3.68 (t, 2H), 3.36 (s, 3H), 2.15 (s, 3H).

The above-described method (Example 2) was repeated to react benzyl 2-amino-5-bromo-3-methylbenzoate (3.00 g, 7.38 mmol) with copper cyanide (0.772 g, 7.98 mmol) in N-methylpyrrolidone at 170° C. for 6 hours. Following working up similar to Example 2, additional extraction with ethyl acetate, washing with aqueous 5% ethylenediamine solution and column chromatography, benzyl 2-amino-5-cyano-3-methylbenzoate (1.00 g, 47.9% of theory, 97.0 area % LC) was obtained as a pale brown solid.

$^1$H NMR (600 MHz, (CDCl$_3$): δ=8.16 (s, 1H), 7.44-7.35 (m, 6H), 6.40 (s, 2H), 5.33 (s, 2H), 2.17 (s, 3H).

Example 3

2-Amino-5-cyano-N,3-dimethylbenzamide

Methylamine (117 g, 3.77 mol) is introduced into a solution of ethyl 2-amino-5-cyano-3-methylbenzoate (50 g, 0.251 mol) in methanol (175 mL), sodium methoxide (1.13 g, 30% strength in methanol, 6.28 mmol) is added and the reaction mixture is stirred overnight at room temperature. Thereafter, 100 ml of 22% strength NaOH are added and the batch is cooled down to 10° C. The suspension obtained is filtered and the solid obtained is washed once with 1:1 methanol:water and then with 50 mL of water. The solid is dried at 50° C. in a vacuum drying cabinet. 2-Amino-5-cyano-N,3-dimethylbenzamide is isolated as a slightly beige solid. Yield: 80.3% of theory, purity: 94.9% quantitative LC, 73 ppm Cu).

$^1$H NMR (600 MHz, (CD$_3$CN): δ=7.65 (d, 1H), 7.38 (s, 1H), 6.91 (br s, 1H), 6.52 (br s, 2 H), 2.82 (d, 3H), 2.12 (s, 3H).

The above-described method (Example 3) was repeated to stir pentyl 2-amino-5-cyano-3-methylbenzoate (1.50 g, mmol) with methylamine (10.8 g, mmol, 40% in methanol) and sodium methoxide (441 mg, 0.12 mmol, 30% in methanol) at room temperature for 18 hours. The entire reaction batch was vacuum distilled and stirred with diisopropyl ether. 2-Amino-5-cyano-N,3-dimethylbenzamide (0.79 g, 70.6% of theory, 96.4 area % LC) was obtained as a brown solid.

The above-described method (Example 3) was repeated to stir hexyl 2-amino-5-cyano-3-methylbenzoate (1.40 g, 4.89 mmol) with methylamine (10.8 g, 139 mmol, 40% in methanol) and sodium methoxide (441 mg, 0.12 mmol, 30% in methanol) at room temperature for 18 hours. The entire reaction batch was vacuum distilled and stirred with diisopropyl ether. 2-Amino-5-cyano-N,3-dimethylbenzamide (0.75 g, 75.8% of theory, 93.6 area % LC) was obtained as a brown solid.

The above-described method (Example 3) was repeated to stir 2-ethylhexyl 2-amino-5-cyano-3-methylbenzoate (1.00 g, 3.09 mmol) with methylamine (3.60 g, 46.3 mmol, 40% in methanol) and one drop of sodium methoxide (30% in methanol) at room temperature for 18 hours. The entire reaction batch was vacuum distilled and 2-amino-5-cyano-N,3-dimethylbenzamide (730 mg, 91.4% of theory, 73.1 area % LC) was obtained as a brown solid.

The above-described method (Example 3) was repeated to stir ethyl 2-amino-5-cyano-3-methylbenzoate (0.50 g, 2.40 mmol) with methylamine (3.73 g, 48 mmol, 40% in methanol) and sodium methoxide (22 mg, 30% in methanol) at room temperature for 18 hours. The entire reaction batch was vacuum distilled and 2-amino-5-cyano-N,3-dimethylbenzamide (0.44 g, 95.9% of theory, 99.0 area % LC) was obtained as a pale brown solid.

The above-described method (Example 3) was repeated to stir ethane-1.2-diyl 2-amino-5-cyano-3-methylbenzoate (20 mg, 0.04 mmol) with methylamine (5.40 g, 69.5 mmol, 40% in methanol) and one drop of sodium methoxide (30% in methanol) at room temperature for 18 hours. The entire reaction batch was vacuum distilled and following purification by column chromatography, 2-amino-5-cyano-N,3-dimethylbenzamide (8 mg, 47.2% of theory, 93.1 area % LC) was obtained as a pale brown solid.

The above-described method (Example 3) was repeated to stir hexane-1.6-diyl 2-amino-5-bromo-3-methylbenzoate) (220 mg, 0.4 mmol) with methylamine (2 g, 25.7 mmol, 40% in methanol) and one drop of sodium methoxide (30% in methanol) at room temperature for 18 hours. The entire reaction batch was vacuum distilled and following purification by column chromatography, 2-amino-5-cyano-N,3-dimethylbenzamide (61 mg, 50.5% of theory, 94.6 area % LC) was obtained as a brown solid.

The above-described method (Example 3) was repeated to stir 2-methoxyethyl 2-amino-5-cyano-3-methylbenzoate (200 mg, 0.81 mmol) with methylamine (5.40 g, 69.5 mmol, 40% in methanol) and one drop of sodium methoxide (30% in methanol) at room temperature for 18 hours. The entire reaction batch was vacuum distilled and following purification by column chromatography, 2-amino-5-cyano-N,3-dimethylbenzamide (150 mg, 95.0% of theory, 97.8 area % LC) was obtained as a pale brown solid.

The above-described method (Example 3) was repeated to stir 2-benzyl 2-amino-5-cyano-3-methylbenzoate (1.00 g, 3.75 mmol) with methylamine (4.78 g, 61.6 mmol, 40% in methanol) and one drop of sodium methoxide (30% in methanol) at room temperature for 18 hours. The entire reaction batch was vacuum distilled and following purification by column chromatography, 2-amino-5-cyano-N,3-dimethylbenzamide (616 mg, 85.4% of theory, 98.4 area % LC) was obtained as a colourless solid.

The invention claimed is:

1. A process for preparing 2-amino-5-cyano-N,3-dimethylbenzamide of formula (I)

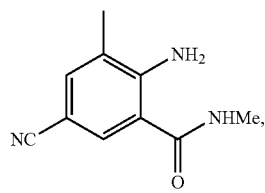
(I)

comprising reacting
(A) 2-amino-5-cyano-3-methylbenzoic esters of formula (II)

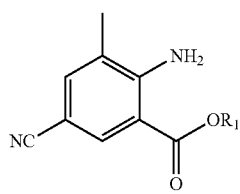
(II)

where
R$^1$ represents pentyl, hexyl, 2-ethylhexyl, methoxyethyl or benzyl,
or
(B) 2-amino-5-cyano-3-methylbenzoic diesters of formula (III)

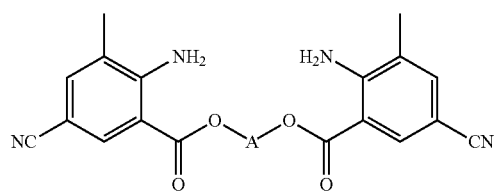
(III)

where
A represents alkylene or alkyloxyalkylene,
with MeNH$_2$.

2. The process according to claim 1, wherein a 2-amino-5-cyano-3-methylbenzoic ester of formula (II) and/or a 2-amino-5-cyano-3-methylbenzoic diester of formula (III) is reacted with MeNH$_2$ by using at least one base.

3. The process according to claim 1, wherein a compound of formula (I) is obtained by reacting a 2-amino-5-cyano-3-methylbenzoic ester of formula (II).

4. The process according to claim 1, wherein a compound of formula (I) is obtained by reacting a 2-amino-5-cyano-3-methylbenzoic diester of formula (III).

5. The process according to claim 2, wherein the base is selected from the group consisting of sodium amide, sodium hydride, sodium hydroxide, sodium cyanide, potassium cyanide, potassium carbonate, sodium carbonate, caesium carbonate, sodium methoxide and triethylamine.

6. The process according to claim 1, wherein a 2-amino-5-cyano-3-methylbenzoic ester of formula (II) is obtained by reacting a compound of formula (IV)

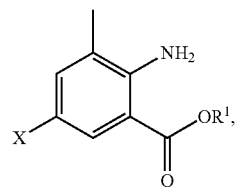
(IV)

with CuCN, where X represents Br or I,
and said compound of formula (IV) is obtained by reacting a compound of formula (VI)

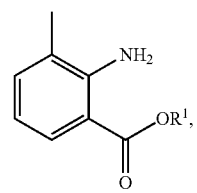
(VI)

with a mixture of HBr/H$_2$O$_2$.

7. The process according to claim 1, wherein a 2-amino-5-cyano-3-methylbenzoic diester of formula (III) is obtained by reacting a compound of formula (V)

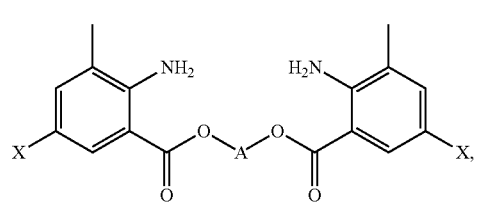
(V)

with CuCN, where X represents Br or I,
and said compound of formula (V) is obtained by reacting a compound of formula (VII)

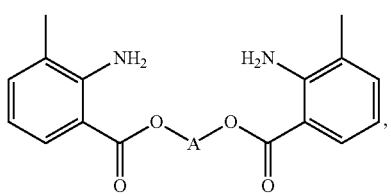
(VII)

with a mixture of HBr/H$_2$O$_2$.

8. The process according to claim 6, wherein from 0.8 mol to 1.4 mol of copper(I) cyanide is used per 1 mol of compound of formula (IV).

9. The process according to claim 6, wherein copper(I) cyanide is used in N,N-dimethylformamide, N,N-dimethylacetamide, N-methylformanilide, N-methylpyrrolidone, hexamethylphosphoramide or dimethyl sulphoxide as solvent.

10. The process according to claim 2, wherein a compound of formula (I) is obtained by reacting a 2-amino-5-cyano-3-methylbenzoic diester of formula (III).

11. The process according to claim 5, wherein a compound of formula (I) is obtained by reacting a 2-amino-5-cyano-3-methylbenzoic diester of formula (III).

12. The process according to claim 7, wherein from 0.8 mol to 1.4 mol of copper(I) cyanide is used per 1 mol of compound of formula (V).

13. The process according to claim 7, wherein copper(I) cyanide is used in N,N-dimethylformamide, N,N-dimethylacetamide, N-methylformanilide, N-methylpyrrolidone, hexamethylphosphoramide or dimethyl sulphoxide as solvent.

14. The process according to claim 4, wherein A represents ethylene or hexylene.

15. The process according to claim 3, wherein R1 is benzyl.

16. The process according to claim 3, wherein R1 is methoxy ethyl.

17. The process according to claim 3, wherein R1 is pentyl, hexyl, or 2-ethylhexyl.

* * * * *